(12) United States Patent
Genna et al.

(10) Patent No.: US 10,450,205 B2
(45) Date of Patent: Oct. 22, 2019

(54) METAL ORGANIC FRAMEWORK WITH PERFLUORINATED LINKER

(71) Applicant: Youngstown State University, Youngstown, OH (US)

(72) Inventors: Douglas T. Genna, Cortland, OH (US); Mariah DeFuria, Canfield, OH (US)

(73) Assignee: Youngstown State University, Youngstown, OH (US)

( * ) Notice: Subject to any disclaimer, the term of this patent is extended or adjusted under 35 U.S.C. 154(b) by 213 days.

(21) Appl. No.: 15/410,813

(22) Filed: Jan. 20, 2017

(65) Prior Publication Data

US 2017/0204118 A1    Jul. 20, 2017

Related U.S. Application Data

(60) Provisional application No. 62/280,769, filed on Jan. 20, 2016.

(51) Int. Cl.
| | | |
|---|---|---|
| *C02F 1/28* | (2006.01) | |
| *B01D 15/00* | (2006.01) | |
| *C02F 1/00* | (2006.01) | |
| *C02F 1/68* | (2006.01) | |
| *C07F 5/00* | (2006.01) | |
| *B01J 20/26* | (2006.01) | |
| *C02F 101/32* | (2006.01) | |
| *C02F 103/34* | (2006.01) | |

(52) U.S. Cl.
CPC ............. *C02F 1/285* (2013.01); *B01D 15/00* (2013.01); *C02F 1/00* (2013.01); *C02F 1/281* (2013.01); *C02F 1/683* (2013.01); *C07F 5/003* (2013.01); *B01J 20/262* (2013.01); *C02F 2101/32* (2013.01); *C02F 2101/327* (2013.01); *C02F 2103/343* (2013.01); *C02F 2303/18* (2013.01)

(58) Field of Classification Search
None
See application file for complete search history.

(56) References Cited

FOREIGN PATENT DOCUMENTS

CN     102 249 363 A     11/2011

OTHER PUBLICATIONS

Yang et al. (J. Ann. Chem. Soc., 2011, 133, 18094-18097). (Year: 2011).*
C.W. Abney et al., "Metal Organic Framework Templated Inorganic Sorbents for Rapid and Efficient Extraction of Heavy Metals", Advanced Materials, vol. 26, Oct. 27, 2014, pp. 7993-7997.
Melanie Werker et al., Two Anhydrous Salts of Tetrafluoroterephthalic Acid (H2tF-BDC): K2tF-BDC and Rb2tF-BDC, Zeitschrift für anorganische und allgemeine Chemie, vol. 639, No. 14, Oct. 25, 2013, pp. 2487-2492.

(Continued)

*Primary Examiner* — Clare M Perrin
(74) *Attorney, Agent, or Firm* — Fay Sharpe LLP

(57) ABSTRACT

A metal organic framework includes metal-containing secondary building units and perfluorinated linkers (e.g., pefluorinated arene linkers, perfluorinated heteroarene linkers, etc.). The metal may be copper, zinc, hafnium, zirconium, aluminum, gallium, or indium. A method for removing contaminants from wastewater may utilize the metal organic framework. The contaminants may include arenes.

13 Claims, 4 Drawing Sheets

(56) References Cited

OTHER PUBLICATIONS

Benedikt Dolfus et al., "[Li2(tF-BDC)(DMF)2]: A New Alkali Metal Salt of Tetrafluoroterephthalic Acid (H2tF-BDC)", Z. Anorg. Allg. Chem., vol. 640, No. 7, Feb. 12, 2014, pp. 1235-1238.
International Search Report and Written Opinion of corresponding International Application No. PCT/US2017/014211, dated Apr. 11, 2017, 12 pages.

* cited by examiner

METAL ORGANIC FRAMEWORK WITH PERFLUORINATED LINKER

CROSS-REFERENCE TO RELATED APPLICATIONS

The application claims the benefit of U.S. Provisional Application Ser. No. 62/280,769, filed Jan. 20, 2016 and titled "Metal Organic Framework with Group 13 Metal and Perfluorinated Arene Linker", which is hereby incorporated by reference herein in its entirety.

BACKGROUND

The present disclosure relates to metal organic frameworks. Methods for making the frameworks and methods for removing contaminants from water using the frameworks are also disclosed.

According to the World Health Organization, pharmaceutical contamination of drinking water is an emerging problem. By some estimates, almost 25% of the world's rivers and lakes are contaminated. Although current contaminant levels are generally below therapeutic thresholds, the effects of prolonged exposure at low dosages are unknown. Pharmaceutical contamination could potentially affect aquatic life in addition to humans.

Some drugs (e.g., tetracycline, ciprofloxacin, and 17α-ethynylestradiol) are not easily degraded via conventional water treatment methods. For example, reverse osmosis and membrane filtration may not remove parts per million (ppm) levels of contaminants. The European Union recently finished the Enzymatic Decontamination Technology (ENDE-Tech) project. This $3.5 million project aimed at developing a commercial technology for the enzymatic degradation of waste pharmaceuticals but did not deliver a commercial product.

In addition to pharmaceuticals, other contaminants (e.g., polycyclic aromatic hydrocarbons) may be present in water. The contaminants may result from incomplete combustion, industrial effluents, and chemical spills such as the Deepwater Horizon incident. Chronic exposure to polycyclic aromatic hydrocarbons has been linked to carcinogenesis and developmental disorders in humans.

Common water treatment techniques (traditionally designed for parasite and microbe removal) such as the activated sludge process are capable of removing some of these contaminants from water streams. However, batch and site disparities in sludge quality are notorious and have led to mixed results in water purification. Furthermore, approaches such as the activated sludge method, although feasible on a plant scale, may not be feasible for deployment to individual users in the field or during site specific catastrophic events.

A more practical alternative would be a non-biologic based alternative that is more reproducible over multiple theaters of deployment. It would be desirable to develop new systems and methods for decontaminating water.

BRIEF DESCRIPTION

The present disclosure relates to metal organic frameworks and methods for making and using the same.

Disclosed, in various embodiments, is a metal organic framework including: secondary building units having a metal or metal cluster or polymeric infinite-chain; and a perfluorinated linker (e.g., a perfluorinated arene linker, a perfluorinated heteroarene linker, etc.).

The metal may be a group 13 metal and may be selected from the group consisting of aluminum, gallium, and indium.

In other embodiments, the metal is selected from the group consisting of copper, zinc, hafnium, and zirconium.

In some embodiments, the perfluorinated arene linker is

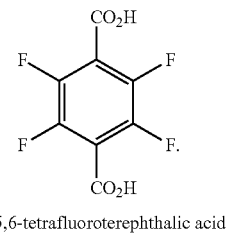

2,3,5,6-tetrafluoroterephthalic acid

Methods for using the metal organic frameworks are also disclosed. An exemplary method for treating water containing a contaminant includes contacting the water with the metal organic framework.

In some embodiments, the contaminant is an arene or a heteroarene.

The contaminant may be a pharmaceutical compound such as tetracycline, ciprofloxacin, or 17α-ethynylestradiol.

In some embodiments, the method further includes removing the metal organic framework containing the contaminant from the water.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
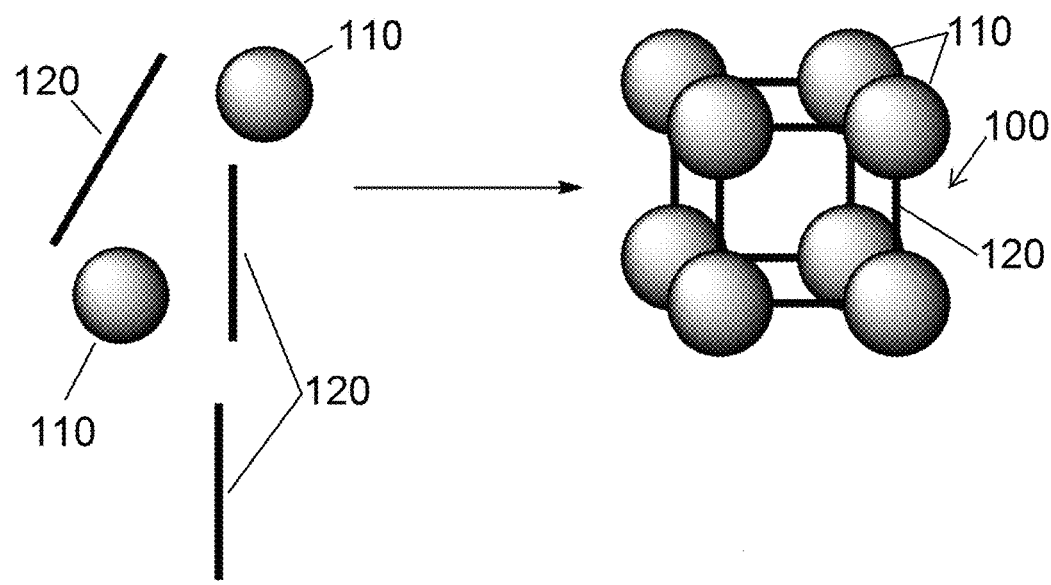
FIG. 1 illustrates the formation of a metal organic framework in accordance with some embodiments of the present disclosure.

A more complete understanding of the devices and methods disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. In the following specification and the claims which follow, reference will be made to a number of terms, which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases that require the presence of the named ingredients/steps and permit the presence of other ingredients/steps. However, such description should be construed as also describing compositions, mixtures, or processes as "consisting of" and "consisting essentially of" the enumerated ingredients/steps, which allows the presence of only the named ingredients/steps, along with any impurities that might result therefrom, and excludes other ingredients/steps.

Unless indicated to the contrary, the numerical values in the specification should be understood to include numerical values which are the same when reduced to the same number of significant figures and numerical values which differ from the stated value by less than the experimental error of the conventional measurement technique of the type used to determine the particular value.

All ranges disclosed herein are inclusive of the recited endpoint and independently combinable. The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints.

For the recitation of numeric ranges herein, each intervening number there between with the same degree of precision is explicitly contemplated.

Metal organic frameworks are materials in which metal-to-organic ligand interactions yield coordination networks. The frameworks include metal-containing secondary building units and organic linkers. The metal-containing secondary building units may consist of single metal ions or may be clusters that include metals and other elements. The secondary building unit may also be referred to as an inorganic node.

FIG. 1 illustrates a metal organic framework 100 in accordance with some embodiments of the present disclosure. The metal organic framework 100 includes secondary building units 110 and linkers 120. The secondary building units 110 contain a metal (e.g., a group 13 metal). In some embodiments, the secondary building units 110 consist of a metal ion. In other embodiments, the secondary building units 110 are clusters. The linkers 120 are perfluorinated linkers (e.g., perfluorinated arene linkers, perfluorinated heteroarene linkers, etc.). The linker of the present disclosure is referred to as "perfluorinated" because it contains no C—H bonds, only C—F bonds.

In some embodiments, the linker 120 is selected from

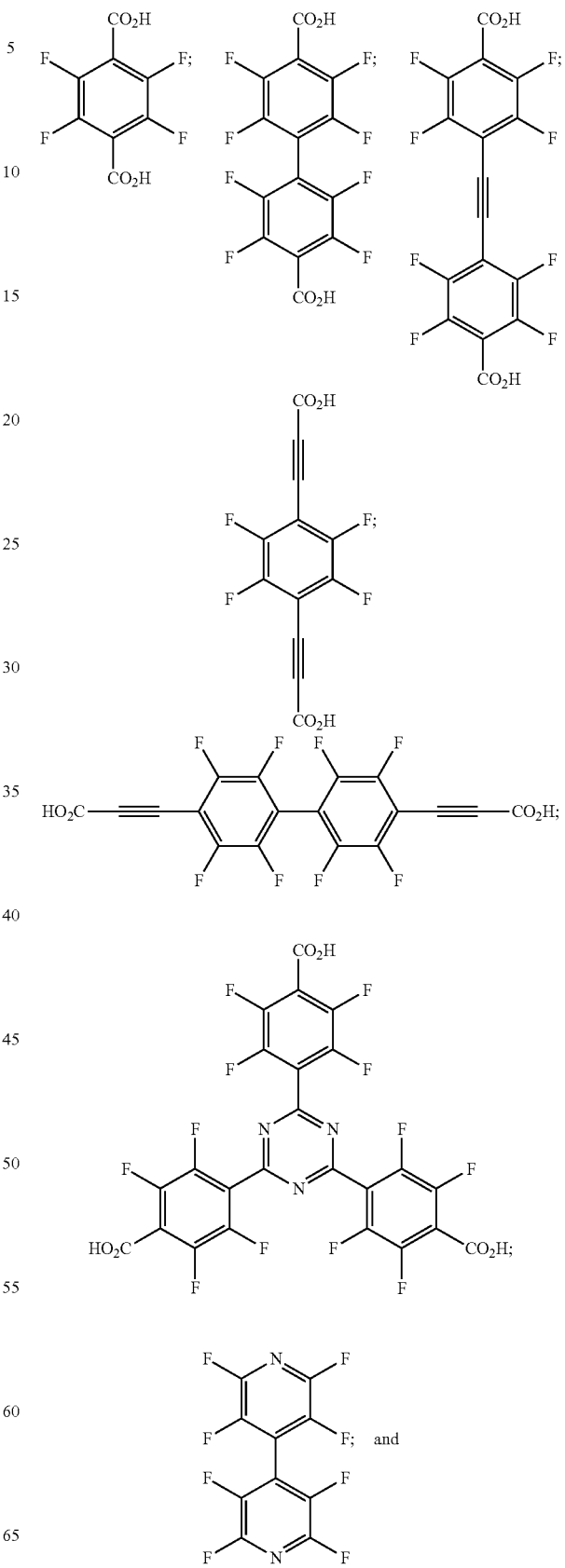

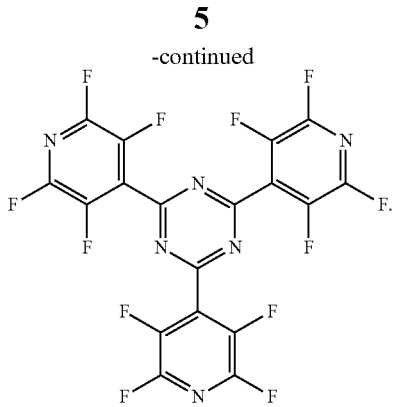

In some embodiments, only one linker compound is included. In other embodiments, multiple linker compounds are included.

The use of alkyne spacers allows for easy linker synthesis via Sonogashira couplings and for potential modulation/oligomer extension in which each linker can be dimerized or trimerized in order to create longer linkers prior to framework synthesis.

When the secondary building units 110 are clusters, the clusters may include the general formula $M(L)_{n-x}(Y)_x$, wherein M is a metal and may be selected from Zr, In, Ga, or Al; L may be selected from carboxyl groups, hydroxyl groups, or amine groups; and Y may be selected from $H_2O$, OH, halogens, or amines. L and Y may also be bridging or non-bridging ligands and can bind a single metal atom with a hapticity ranging from about 1 to about 5. Non-limiting examples include $[M(\mu-O_2CR)_2(\mu-OH)]_\infty$, trimeric $[M_3O(O_2CR)_6(H_2O)_3]^+$ and derivatives thereof, wherein M is a metal.

Another example of a secondary building unit is a metal paddlewheel of $M_2(O_2CR)_4$, wherein M is a metal. In some embodiments, the metal is copper, zinc, or zirconium.

Another example of a secondary building unit is a $M_6O_6$, wherein M is a metal. In some embodiments, the metal is zirconium or hafnium.

In some embodiments, the metal organic framework includes a secondary building unit and from about 4 to about 12 organic linkers.

Figure 2:
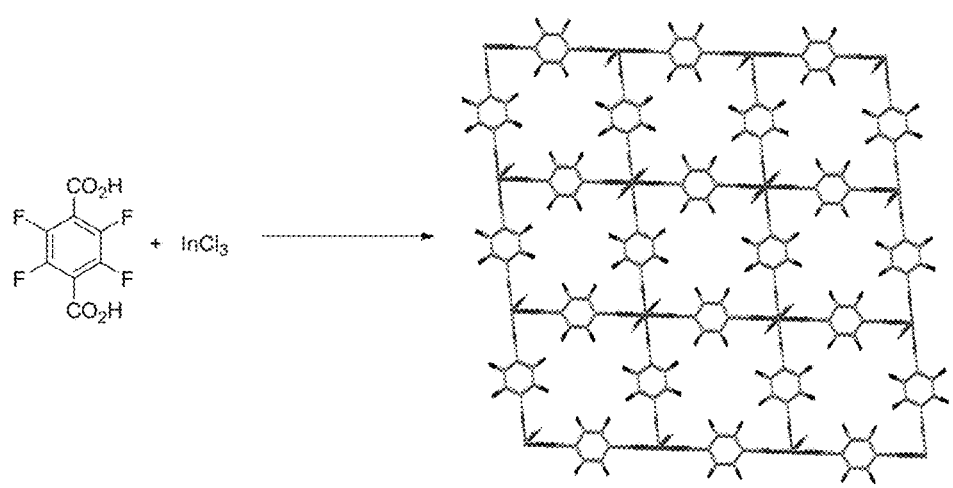
FIG. 2 illustrates a reaction for forming a metal organic framework in accordance with some embodiments of the present disclosure.
Figure 3:
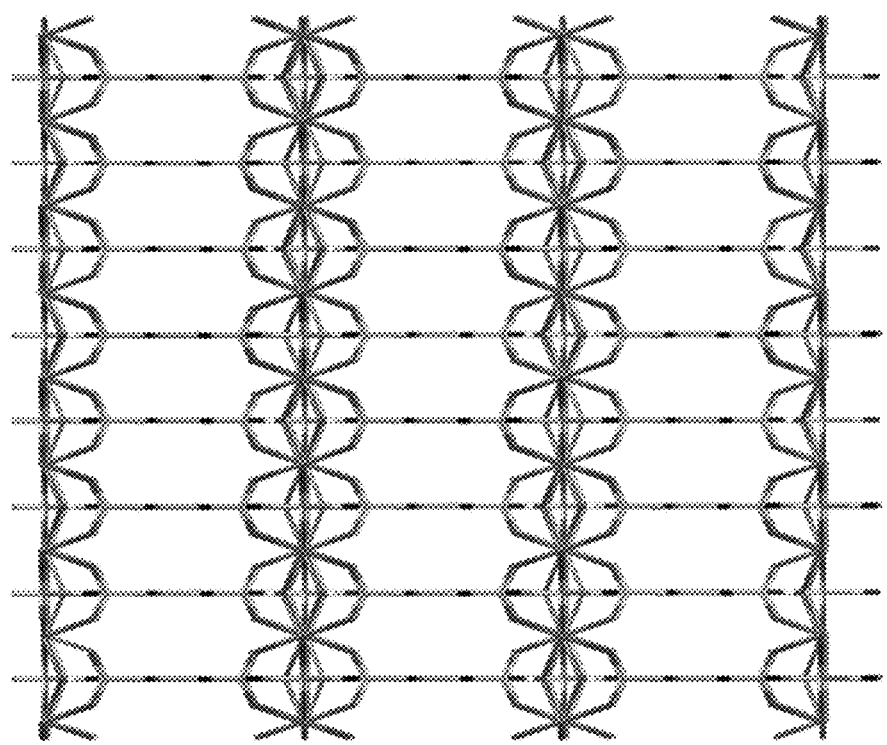
FIG. 3 illustrates a metal organic framework in accordance with some embodiments of the present disclosure.

FIGS. 2 and 3, which are described in more detail below, are examples of nodes with $[In(\mu-O_2CR)_2(\mu-OH)]_\infty$ secondary building units.

FIG. 2 illustrates a reaction for forming a metal organic framework in accordance with some embodiments of the present disclosure. The reactants are 2,3,5,6-tetrafluoroterephthalic acid and indium (III) chloride. However, other reactants may also be used as long as the linker is perfluorinated and the secondary building units contain a metal. In some embodiments, the metal is copper, zinc, hafnium, zirconium, aluminum, gallium, or indium.

In some embodiments, the carboxyl groups in 2,3,5,6-tetrafluoroterephthalic acid are replaced with hydroxyl groups or amine groups. Non-limiting examples of amines include heterocyclic amines, triazoles, and free amines.

In some embodiments, the indium in indium (III) chloride is replaced with a different metal and/or the chloride is replaced with a different halide or ligand.

FIG. 3 illustrates a perspective view of a metal organic framework in accordance with some embodiments of the present disclosure.

Figure 4:
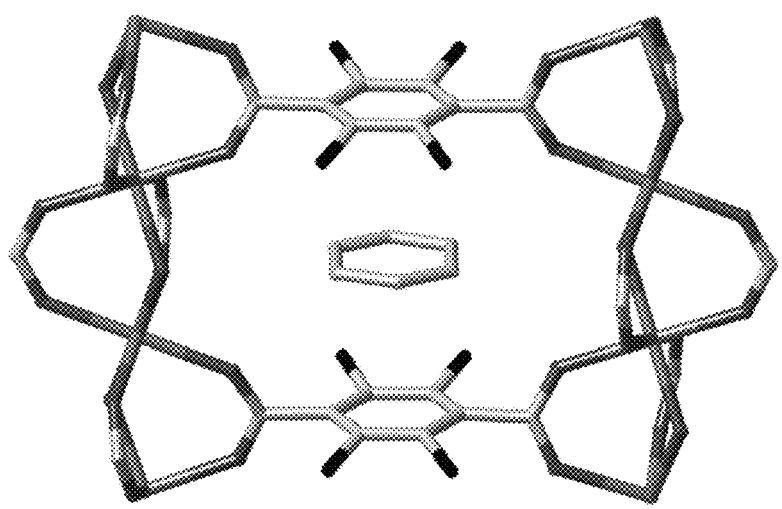
FIG. 4 illustrates an expanded view of a portion of a metal organic framework in accordance with some embodiments of the present disclosure.

FIG. 4 illustrates an expanded view of a portion of a metal organic framework in accordance with some embodiments of the present disclosure.

Figure 5A:
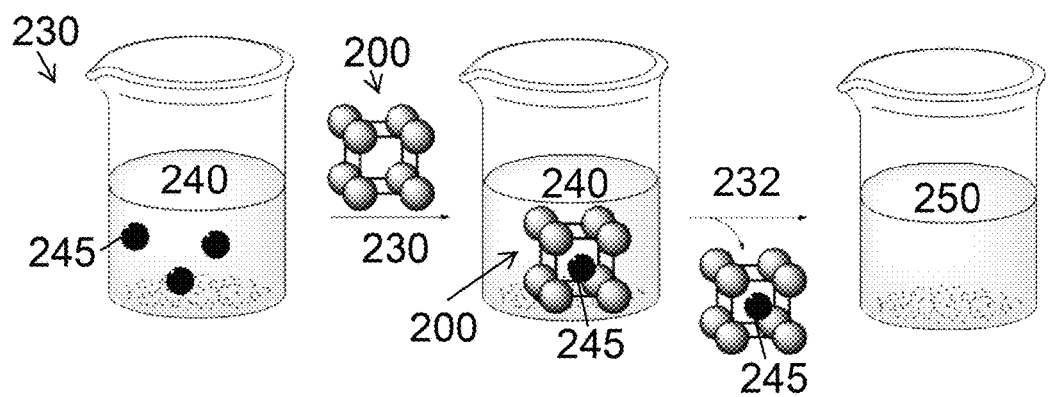
FIGS. 5A and 5B are schematic illustrations of a decontamination method in accordance with some embodiments of the present disclosure.
Figure 5B:
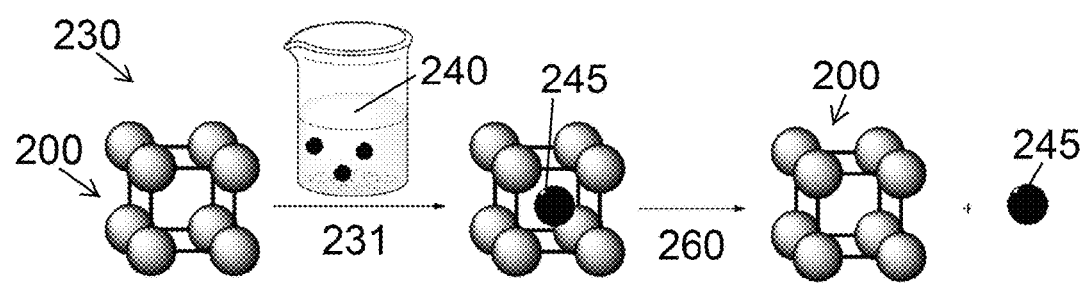

FIGS. 5A and 5B illustrate a method 230 for decontaminating water in accordance with some embodiments of the present disclosure. The method 230 includes providing 231 a metal organic framework 200 to wastewater 240 containing contaminants 245. The method 230 further includes removing (e.g., filtering out) 232 the metal organic framework 200 with contaminants 245 to produce clean water 250. The removal may be a batch process or a continuous process.

In the batch process, the metal organic framework can be added to a fixed volume of contaminated water. After a period of time, the metal organic framework can be removed (e.g., via filtration) with at least a portion of the contaminants contained therein. Depending on solution concentration loading, contaminant removal may take from about an hour up to several days. For example, a 2 mL solution containing about 10,000 ppm tetracycline can be decontaminated down to about 9,200 ppm after 5 days using about 50 mg of the metal organic framework. However, the initial contamination concentration may generally be lower (e.g., from about 1 ppm to about 2 ppm).

In the continuous process, the metal organic framework can be supplied to a stream of contaminated water and removed after a fixed period of time.

Optionally, the metal organic framework containing the contaminants can be recycled. The recycling may include removing the contaminants from the metal organic framework, thereby rendering the metal organic framework suitable for another removal step. The recycling may be performed in the field or in a laboratory setting. The recycling may include washing with solvent, heating in the solid state, heating in a solvent, or some combination thereof. In some embodiments, the contaminant may be removed through a series of solvent washing steps. The solvent may be ethanol.

Figure 6A:
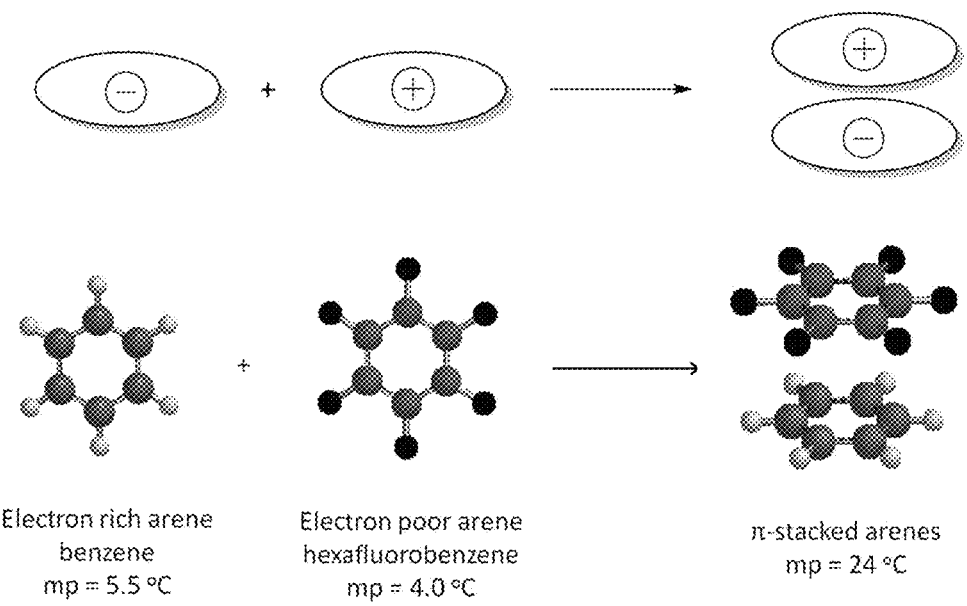
FIGS. 6A and 6B illustrate π-π stacking.
Figure 6B:
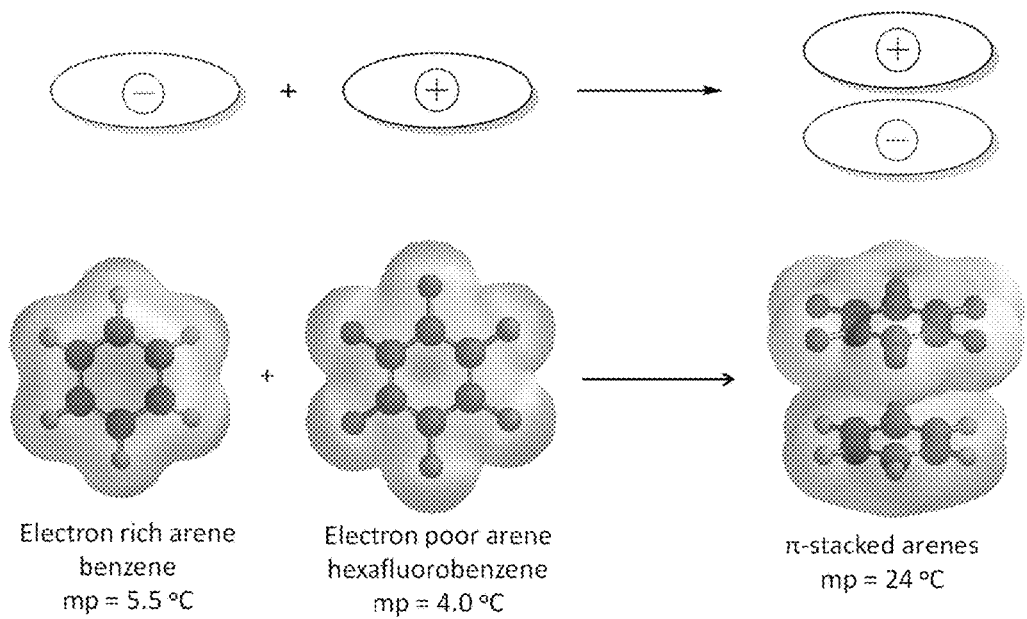

FIGS. 6A and 6B illustrate π-π stacking between benzene and hexafluorobenzene. In some embodiments, the contaminant is an arene compound. Without wishing to be bound by theory, it is believed that π-π interactions between an electron-poor linker (e.g., a perfluorinated arene) and an electron-rich contaminant (e.g., an arene compound) will facilitate removal of the contaminant from a contaminated water source. π-π stacking (which may also be referred to as aromatic stacking or aromatic-aromatic interaction) refers to a noncovalent attractive force between two aromatic rings.

The contaminant may be a pharmaceutical compound. In some embodiments, the pharmaceutical compound removed from the water is selected from

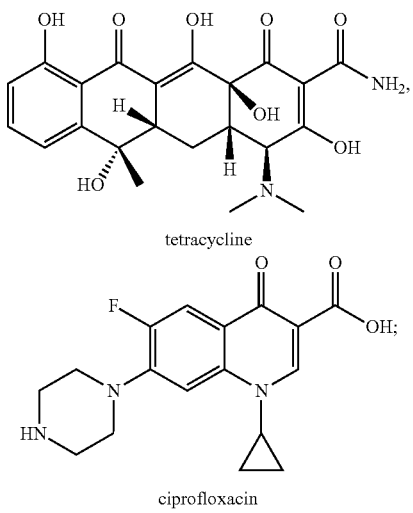

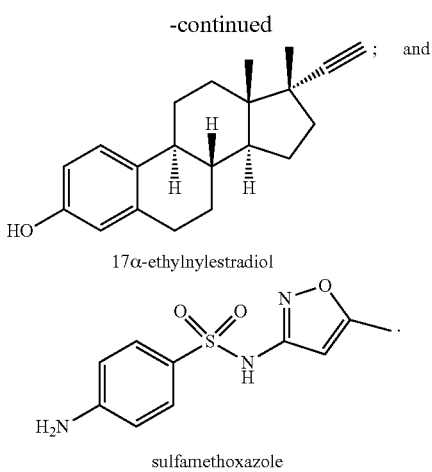

17α-ethylnylestradiol sulfamethoxazole

However, the decontamination and water treatment methods of the present disclosure are not limited to embodiments wherein the contaminants are pharmaceutical compounds. In some embodiments, the contaminants have resulted from incomplete combustion, industrial effluent, or a chemical spill.

The systems and methods of the present disclosure may be used to remove polycyclic aromatic hydrocarbons, benzene, naphthalene, anthracene, pyrene, and/or combinations thereof and/or their derivatives.

In some embodiments, the systems and methods are used to treat water contaminated with at least one pharmaceutical compound and at least of polycyclic aromatic hydrogen.

The following examples are provided to illustrate the devices and methods of the present disclosure. The examples are merely illustrative and are not intended to limit the disclosure to the materials, conditions, or process parameters set forth therein.

EXAMPLES

Example 1: Metal Organic Framework Production

Indium (III) chloride and 2,3,5,6-tetrafluoroterephthalic acid were reacted to form a metal organic framework. To a pre-mixed solution of N,N-dimethylformamide (DMF) (4.75 mL), 2-propanol (85.50 mL), and deionized water (4.75 mL) was added 2,3,5,6-tetrafluoroterephthalic acid (0.595 g, 2.50 mmol, 1.00 equiv) and $InCl_3$ (1.10 g, 5.00 mmol, 2.00 equiv) in that order. The resulting solution was sonicated for 6-7 minutes until complete dissolution was observed. The solution sat in a hood for 30 minutes covered with Parafilm, which was determined to produce larger crystals than no wait period. The clear solution was then filtered through a GE-brand 25 mm PVDF syringe filter in 5 mL portions into 20 mL scintillation vials. The scintillation vials were sealed with Teflon-lined caps and placed in an 80° C. oven for 72 h. The vials were removed from the oven and allowed to cool to room temperature. The colorless crystals were combined into one 4 mL vial by drawing up both crystals and mother liquor using a pipette. The mother liquor was decanted away from the crystals which were then washed with DMF (3×2 mL). Crystals of the framework material washed with DMF (3×2 mL) were dried under vacuum at room temperature for a minimum of 18 h.

Example 2: Pharmaceutical Sequestration

To a 4 mL vial containing 2.00 mL deuterium oxide was added tetracycline HCl (0.020 g, 0.042 mmol, 1.00 equiv). The solution was manually shaken until dissolution was observed. Dried framework material (0.0500 g) was then added to the golden yellow solution. The vial was placed on a Thermo Scientific MaxQ 2000 shaker (~100 RPM) for five days. The doping liquid was then removed via pipette and set aside for NMR analysis. The yellow crystals were rinsed with deuterium oxide (3×2 mL); the second rinse portion was used to transfer the crystals to a new 4 mL vial, and the crystals soaked in the third portion overnight. All washings were combined and analyzed via $^1H$ NMR using tetrahydrofuran (3.4 μL, 0.042 mmol, 1.0 equiv) as a standard. Separately the yellow crystals were digested using a 1:1 mixture by volume of $DCl:CD_3OD$ (3.00 mL). The resulting solution was then analyzed using $^1H$ NMR spectroscopy using dichloromethane (2.7 μL, 0.042 mmol, 1.0 equiv) as a standard. NMR analysis indicated approximately ~8% of the starting tetracycline was incorporated into the MOF framework.

The present disclosure has been described with reference to exemplary embodiments. Obviously, modifications and alternations will occur to others upon reading and understanding the preceding detailed description. It is intended that the present disclosure be construed as including all such modifications and alterations insofar as they come within the scope of the appended claims or the equivalents thereof.

The invention claimed is:

1. A method for treating water containing a contaminant, the method comprising:
   contacting the water with a metal organic framework;
   wherein the metal organic framework comprises:
   a secondary building unit comprising a metal; and
   a perfluorinated linker;
   wherein the metal is selected from the group consisting of copper, zinc, hafnium, zirconium, and group 13 metals.
2. The method of claim 1, wherein the metal is selected from the group consisting of copper, zinc, hafnium, and zirconium.
3. The method of claim 1, wherein the metal is the group 13 metals.
4. The method of claim 3, wherein the group 13 metal is selected from the group consisting of aluminum, gallium, and indium.
5. The method of claim 1, wherein the perfluorinated linker is

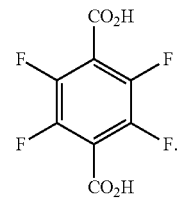

6. The method of claim 1, wherein the secondary building unit consists of a metal ion.
7. The method of claim 1, wherein the contaminant is an arene contaminant.
8. The method of claim 1, wherein the contaminant is a pharmaceutical compound selected from the group consisting of tetracycline, ciprofloxacin, and 17a-ethynylestradiol.
9. The method of claim 1, further comprising removing the metal organic framework containing the contaminant from the water.

10. A method for treating water containing a contaminant, the method comprising:
  contacting the water with a metal organic framework;
  wherein the metal organic framework comprises:
  a secondary building unit comprising a metal; and
  a perfluorinated linker;
  wherein the perfluorinated linker is

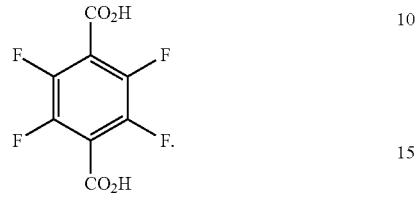

11. The method of claim 10, wherein the metal is selected from the group consisting of copper, zinc, hafnium, and zirconium.

12. The method of claim 10, wherein the metal is a group 13 metal.

13. The method of claim 12, wherein the group 13 metal is selected from the group consisting of aluminum, gallium, and indium.

* * * * *